United States Patent
Gregerson et al.

(10) Patent No.: US 9,462,984 B2
(45) Date of Patent: *Oct. 11, 2016

(54) DIAGNOSTIC IMAGING APPARATUS WITH AIRFLOW COOLING SYSTEM

(71) Applicant: Mobius Imaging, LLC, Ayer, MA (US)

(72) Inventors: Eugene A. Gregerson, Bolton, MA (US); Russell Stanton, Lunenberg, MA (US); Michael Allen, Boxborough, MA (US); Michael Connor, Tyngsboro, MA (US); Scott Coppen, Amesbury, MA (US)

(73) Assignee: MOBIUS IMAGING, LLC, Shirley, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/324,424

(22) Filed: Jul. 7, 2014

(65) Prior Publication Data

US 2014/0378817 A1 Dec. 25, 2014

Related U.S. Application Data

(63) Continuation of application No. 13/025,573, filed on Feb. 11, 2011, now Pat. No. 8,770,839.

(60) Provisional application No. 61/315,462, filed on Mar. 19, 2010.

(51) Int. Cl.
*A61B 6/00* (2006.01)
*F01P 5/02* (2006.01)
(Continued)

(52) U.S. Cl.
CPC ............... *A61B 6/4488* (2013.01); *A61B 6/44* (2013.01); *F01P 5/02* (2013.01); *F01P 5/06* (2013.01);
(Continued)

(58) Field of Classification Search
CPC ........ A61B 6/00; A61B 6/44; A61B 6/4429; A61B 6/4435; A61B 6/4447; A61B 6/4488; A61N 5/00; A61N 5/10; A61N 2005/002; A61N 2005/005; A61N 2005/007; A61N 2005/0632; F01P 1/00; F01P 1/06; F01P 1/08; F01P 5/00; F01P 5/02; F01P 5/06; F01P 5/08; F01P 7/00; F01P 7/02; F01P 11/10
USPC .............. 378/4, 141, 193, 198, 19, 204, 210
See application file for complete search history.

(56) References Cited

U.S. PATENT DOCUMENTS 4,355,410 A 10/1982 Sullins
4,928,283 A 5/1990 Gordon
(Continued)

FOREIGN PATENT DOCUMENTS

EP 0395711 B1 3/1995

OTHER PUBLICATIONS

International Search Report and Written Opinion issued in PCT Application No. PCT/US2011/024531, mailed Apr. 6, 2011.

(Continued)

*Primary Examiner* — Anastasia Midkiff
(74) *Attorney, Agent, or Firm* — The Marbury Law Group, PLLC (57) ABSTRACT

A diagnostic imaging system, which can be a mobile or stationary surgical CT imaging system or an MRI system, comprises an internal airflow cooling system that includes an air intake opening and an air outtake opening that are positioned near the ground and direct air flow away from the sterile surgical field.

38 Claims, 7 Drawing Sheets

(51) Int. Cl.

| | | |
|---|---|---|
| *F01P 5/06* | (2006.01) | |
| *A61N 5/00* | (2006.01) | |
| *A61N 5/06* | (2006.01) | |
| *F01P 1/00* | (2006.01) | |
| *F01P 7/02* | (2006.01) | |
| *F01P 11/10* | (2006.01) | |
| *A61B 6/03* | (2006.01) | |
| *G01R 33/38* | (2006.01) | |

(52) U.S. Cl.
CPC .............. *A61B 6/035* (2013.01); *A61B 6/4405* (2013.01); *A61B 6/4423* (2013.01); *A61B 6/4429* (2013.01); *A61B 34/25* (2016.02); *A61N 2005/002* (2013.01); *A61N 2005/0632* (2013.01); *F01P 1/00* (2013.01); *F01P 7/02* (2013.01); *F01P 11/10* (2013.01); *G01R 33/3804* (2013.01)

(56) References Cited

U.S. PATENT DOCUMENTS

| | | |
|---|---|---|
| 4,969,167 A | 11/1990 | Zupancic et al. |
| 5,146,094 A | 9/1992 | Stark |
| 5,448,607 A | 9/1995 | McKenna |
| 5,448,608 A | 9/1995 | Swain et al. |
| 5,761,269 A | 6/1998 | Sugihara et al. |
| 5,956,383 A | 9/1999 | Kendall |
| 5,982,843 A | 11/1999 | Bailey et al. |
| 6,909,775 B2 | 6/2005 | Ray et al. |
| 6,940,941 B2 | 9/2005 | Gregerson et al. |
| 6,963,632 B2 | 11/2005 | Kendall |
| 7,001,045 B2 | 2/2006 | Gregerson et al. |
| 7,072,445 B2 | 7/2006 | Kendall |
| 7,175,347 B2 | 2/2007 | Tybinkowski et al. |
| 7,311,439 B2 | 12/2007 | Muller |
| 7,410,295 B2 | 8/2008 | Distler et al. |
| 8,770,839 B2 * | 7/2014 | Gregerson et al. ............ 378/199 |
| 2002/0009174 A1 * | 1/2002 | Sasaki ................. 378/4 |
| 2004/0114723 A1 * | 6/2004 | Ray ...................... A61B 6/4488 378/141 |
| 2004/0170254 A1 | 9/2004 | Gregerson et al. |
| 2004/0202287 A1 | 10/2004 | Muller |
| 2004/0228450 A1 | 11/2004 | Mueller |
| 2005/0117698 A1 | 6/2005 | Lacey et al. |
| 2005/0135560 A1 | 6/2005 | Dafni et al. |
| 2009/0041181 A1 | 2/2009 | Krug |
| 2009/0185663 A1 | 7/2009 | Gaines |
| 2009/0232281 A1 * | 9/2009 | Jimbo et al. .................. 378/199 |
| 2010/0172468 A1 | 7/2010 | Gregerson |

OTHER PUBLICATIONS

International Preliminary Report on Patentability issued in PCT Application No. PCT/US2011/024531, mailed Oct. 4, 2012.
Supplementary European Search Report issued in European Patent Application No. 11756688.5 mailed Aug. 13, 2013.

* cited by examiner

DIAGNOSTIC IMAGING APPARATUS WITH AIRFLOW COOLING SYSTEM

CROSS-REFERENCE TO RELATED APPLICATIONS

This application is a continuation of U.S. patent application Ser. No. 13/025,573, filed Feb. 11, 2011, which claims the benefit of U.S. Provisional Application No. 61/315,462, filed Mar. 19, 2010, the entire contents of both of which are incorporated herein by reference.

This application claims the benefit of U.S. Provisional Application No. 61/315,462, filed Mar. 19, 2010, and is related to U.S. application Ser. No. 12/576,681, filed Oct. 9, 2009, and to U.S. Provisional Application No. 61/313,299, filed Mar. 12, 2010. The entire disclosures of the above-referenced applications are incorporated herein by reference.

STATEMENT REGARDING FEDERALLY SPONSORED RESEARCH OR DEVELOPMENT

N/A

BACKGROUND OF THE INVENTION

The present invention relates to a cooling system for a diagnostic imaging apparatus.

A conventional computed tomography (CT) x-ray scanner is a relatively large, stationary device having a fixed bore, and is typically located in a dedicated x-ray room, such as in the radiology department of a hospital. A number of components of the x-ray scanning device, such as the x-ray source and high-voltage generator, are known to generate a large amount of heat during operation of the system. Other components, such as the x-ray detector, are very sensitive to heat. Conventional CT scanners typically include cooling systems to manage heat flow, and ensure that the heat generated by the system does not interfere with the operation of the imaging apparatus. These cooling systems can be relatively large and complex, which is not a problem with conventional systems, which are very large and fixed in place.

It would be desirable to have true X-ray CT functionality in a mobile device that can, for example, easily be moved to different areas of a hospital and can be used at the point of care, such as in an operating room or emergency room. However, making an x-ray CT scanner mobile, while maintaining the same level of functionality as conventional fixed systems, requires substantial changes to overall system architecture. Ideally, a mobile system should be made smaller, more compact and lightweight relative to conventional systems. Moreover, other considerations need to be taken into account where the system is intended to be used in a sterile environment. The conventional techniques for cooling are not well adapted to small and/or mobile imaging devices.

BRIEF SUMMARY OF THE INVENTION

According to one aspect of the invention, a diagnostic imaging system comprises an internal airflow cooling system that includes an air intake opening and an air exhaust opening that are positioned near the ground and direct air flow away from a sterile surgical field. According to some embodiments, the diagnostic imaging system is a mobile or stationary surgical CT imaging system or a magnetic resonance (MR) imaging system.

In certain embodiments, the imaging system includes an air duct system. The imaging system also includes a gantry that is a generally O-shaped housing that contains a plurality of imaging components. The interior housing of the gantry can be in fluid communication with the air duct system at two locations that, in one embodiment, are generally opposed to one another on the gantry. The gantry includes a generally enclosed or sealed interior housing.

In one embodiment, the imaging system further includes a generally C-shaped support gimbal, and the air duct system is at least partially contained within the gimbal. The gimbal supports the gantry, and attaches to the gantry at two opposed ends of the gantry to provide fluid communication between the air duct system and the interior housing of the gantry. In one embodiment, the gimbal is connected to the gantry by a bearing system that includes a through-hole for providing fluid communication between the air duct system and the interior housing of the gantry. The bearing system enables the gantry to tilt with respect to the gimbal upon which it is supported.

In one embodiment, the airflow cooling system includes an air intake opening so that air is allowed to enter the generally C-shaped gimbal close to the ground, and an air exhaust opening wherein the air is allowed to exit the opposite side of generally C-shaped gimbal also close to the ground. The air intake opening is in fluid communication with the interior of the gantry and, in one embodiment, air enters the gantry through a first bearing that attaches the gantry to the gimbal. The airflow passes through the gantry and, in one embodiment, exits the gantry via a second bearing located opposite the first bearing on the gantry, thus allowing the airflow to be directed through the gimbal to the air exhaust opening.

In one embodiment, the gantry includes an airflow bifurcation system that forces airflow entering from a first side of the gantry to be distributed in two directions around the interior of the gantry and to exit through an opening on the opposite side of the gantry. The bifurcation system can include a plurality of bulkheads along the top and bottom paths of the gantry that direct the air along the top and the bottom of the gantry and prevent airflow in the opposing direction. In one embodiment, a plurality of fans are cooperatively associated with the bulkheads to facilitate the airflow in the desired direction.

In one embodiment, a plurality of imaging components are housed within the gantry, and are mounted on a rotor that rotates within the gantry. The rotor rotates around the interior the gantry during imaging procedures (scans), and can rotate to a pre-determined angular position (or "park" position) within the gantry between imaging procedures. The system can be configured such that, when the rotor is in a "park" position, in general, heat sensitive components are provided on the air intake side of the gantry and the less heat sensitive components placed on the air exhaust side of the gantry. In some embodiments, at least some imaging components can be provided on or within the gimbal, with the more heat sensitive components being provided on the air intake side of the gimbal, and the less heat sensitive components being provided on the air exhaust side of the gimbal.

According to another aspect, the heat generating components housed within the gantry are generally provided proximate to the air exhaust opening when the rotor is in a park position.

In other embodiments, a method of imaging uses a diagnostic imaging system having an internal airflow cooling system.

In one embodiment, components within the generally O-shaped gantry are arranged so that the components less susceptible to heating effect are generally placed proximate to one another on a first side of the gantry and the components more susceptible to heating effects are generally placed proximate to one another on a second side of the gantry, opposite the first side.

BRIEF DESCRIPTION OF THE SEVERAL VIEWS OF THE DRAWINGS

Other features and advantages of the present invention will be apparent from the following detailed description of the invention, taken in conjunction with the accompanying drawings of which.

DETAILED DESCRIPTION OF THE INVENTION

Figure 1:
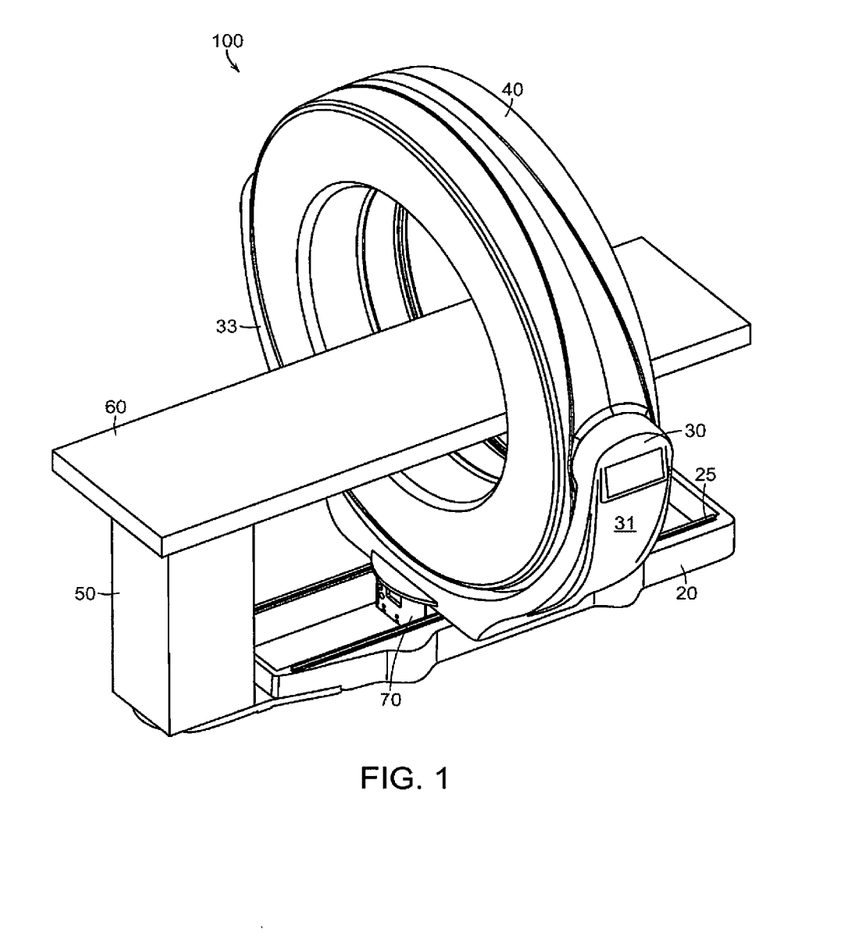
FIG. 1 is a perspective view of an X-ray CT imaging system in accordance with one embodiment of the invention.

Referring to FIG. 1, a mobile imaging system 100 according to one embodiment of the invention includes a mobile base 20, a gimbal 30, a gantry 40, and a pedestal 50. The system 100 includes image collection components, such as a rotatable x-ray source and detector array or stationary magnetic resonance imaging components, that are housed within the gantry 40. The system 100 is configured to collect imaging data, such as, for example x-ray computed tomography (CT) or magnetic resonance imaging (MRI) data, from an object located within the bore of the gantry 40, in any manner known in the medical imaging field. The pedestal 50 is adapted to support a tabletop support 60 that can be attached to the pedestal 50 in a cantilevered manner and extend out into the bore of the gantry 40 to support a patient or other object being imaged.

The gimbal 30 is a generally C-shaped support that is mounted to the top surface of base 20 and includes a pair of arms 31, 33 extending up from base. The arms 31, 33 are connected to opposite sides of gantry 40 so that the gantry ring is suspended above base 20 and gimbal 30.

In certain embodiments, the gimbal 30 and gantry 40 translate with respect to the base 20 to provide an imaging scan. The gimbal 30 includes bearing surfaces that travel on rails 25, as shown in FIG. 1, to provide the translation motion of the gimbal 30 and gantry 20. In one embodiment, a scan drive mechanism drives the translation of the gantry and gimbal relative to the base, and a main drive mechanism drives the entire system in a transport mode. In the embodiment of FIG. 1, both of these functions are combined in a drive system 70 that is located beneath the gimbal 30.

Figure 6:
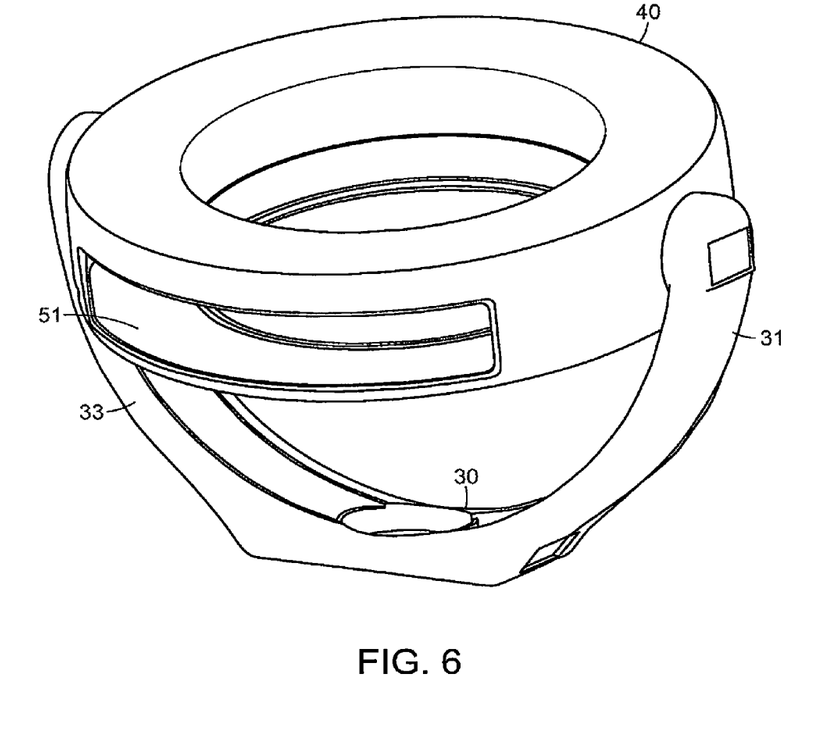
FIG. 6 illustrates a gantry that is tilted and rotated to illustrate an access panel.

In one embodiment, the gimbal 30 and gantry 40 rotate about an axis relative to the base. FIG. 6 illustrates the gimbal 30 and gantry 40 partially rotated. According to another aspect, the gantry 40 can tilt relative to the gimbal 30, as is shown in FIG. 6.

Figure 5:
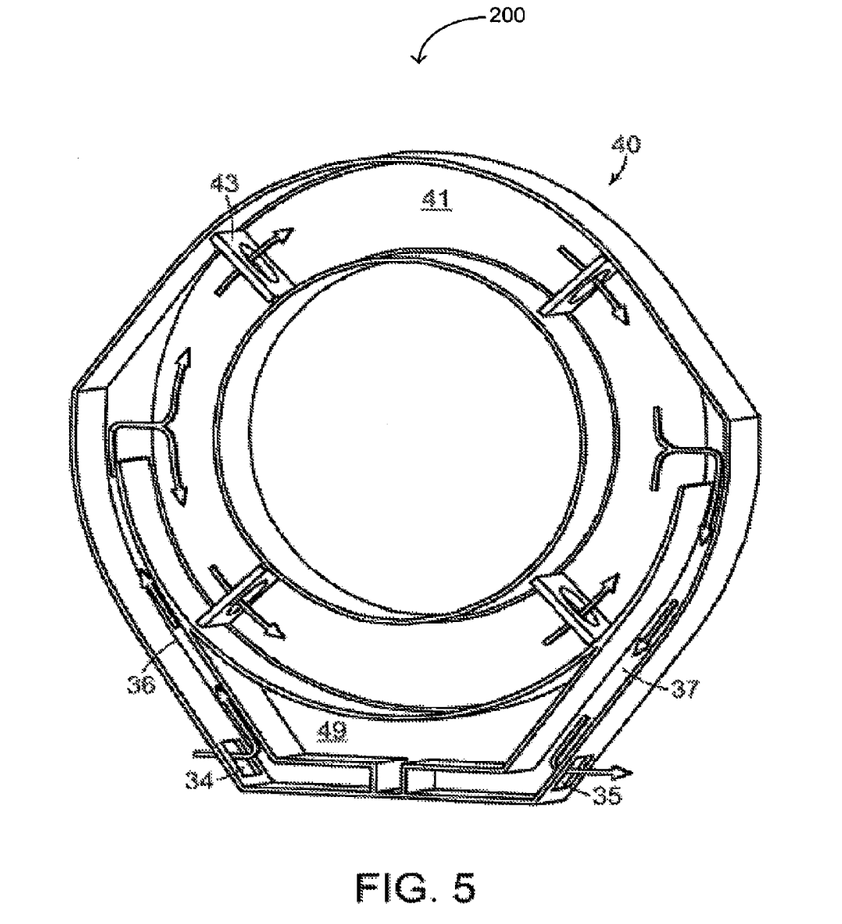
FIG. 5 is a cross-sectional perspective view of a stand-alone gantry with an airflow cooling system according to one embodiment of the invention.

In certain embodiments, the base of the system is omitted, and the gimbal 30 sits directly on the ground to support the gantry 40. In other embodiments, such as shown in FIG. 5, the gimbal is omitted, and the gantry 40 is a stand-alone gantry that sits on the ground.

Figure 2:
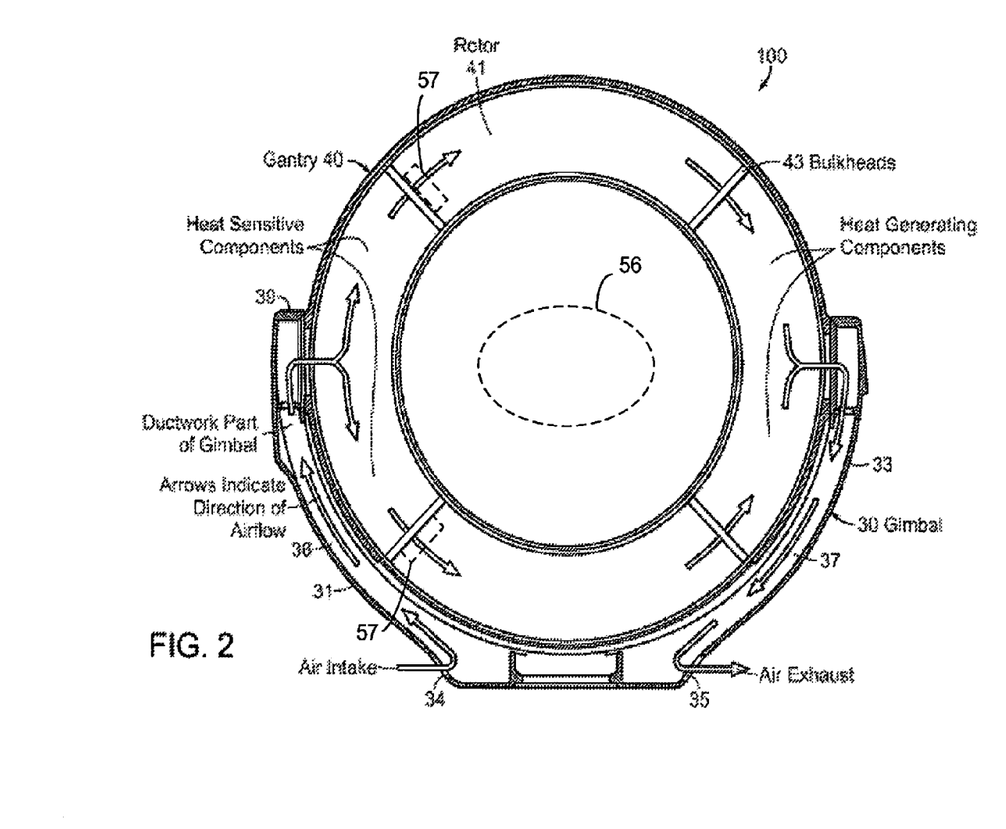
FIG. 2 is a cross-sectional side view of an imaging gantry and gimbal support with an airflow cooling system.

FIG. 2 is a cross-sectional view of the gimbal 30 and gantry 40 according to one embodiment of the invention. The gantry 40 in this embodiment is a generally O-shaped housing that contains a rotor 41 in the interior of the housing. The rotor 41 rotates within the interior of the gantry, as is known, for example, in conventional X-ray CT scanners. A plurality of imaging components, such as an x-ray source and x-ray detector, are mounted to the rotor 41, and thus rotate around the interior of the gantry 40 in coordination with the rotation of the rotor 41. A suitable drive mechanism can drive the rotation of the rotor 41 around the interior of the gantry 40, as is known in the art. The drive mechanism can be controlled by a system controller that controls the rotation and precise angular position of the rotor 41 with respect to the gantry 40, preferably using position feedback data, such as from a position encoder device.

The imaging system further includes an airflow cooling system, as shown in FIG. 2. The airflow cooling system in this embodiment includes an air intake opening 34 and an air exhaust opening 35. Both openings 34, 35 can be located at or near the bottom of the gimbal 30. In one embodiment, the air intake opening 34 and/or the air exhaust opening 35 are located below the patient or object being imaged, generally below the gantry bore, or the gantry housing, and preferably below the area of a surgical sterile field. In the embodiment of FIG. 2, the air exhaust opening 35 is on the opposite side of the gimbal 30 from the air intake opening 34, which helps prevent the generally hotter exhaust air from entering the intake opening 34 and recirculating through the cooling system.

According to one aspect, ambient air is drawn through the air intake opening 34 and up through a duct 36 that extends through the interior one of the arms 31 of the gimbal 30. One or more fans or blowers (not shown) can be provided proximate the intake opening 34 or within the duct 36 to facilitate the flow of air. At the top of the arm 31, the duct 36 is in fluid communication with the interior housing of the gantry 40. The gimbal 30 can be connected to the gantry 40 by a bearing system 39 that enables the "tilt" motion of the gantry (FIG. 6). The bearing system 39 can include a through-hole for providing fluid communication between the air duct 36 and the interior of the gantry 40. This is shown more clearly in FIG. 3.

As the air enters the interior of the gantry 40, the flow of air is bifurcated, as indicated by the arrows, so that a portion of the air flow is distributed to the top side of the gantry and a portion of the air is distributed to the bottom side of the gantry. The two air flows rejoin each other on the opposite side of the gantry 40, where the air then exits the gantry 40 into a duct 37, which extends along the interior of gimbal arm 33. The air then exits the system through exhaust opening 35. One or more fans or blowers (not shown) can be provided proximate the exhaust opening 35 or within the duct 37 to facilitate the flow of air in the direction indicated by the illustrated arrows.

Figure 3:
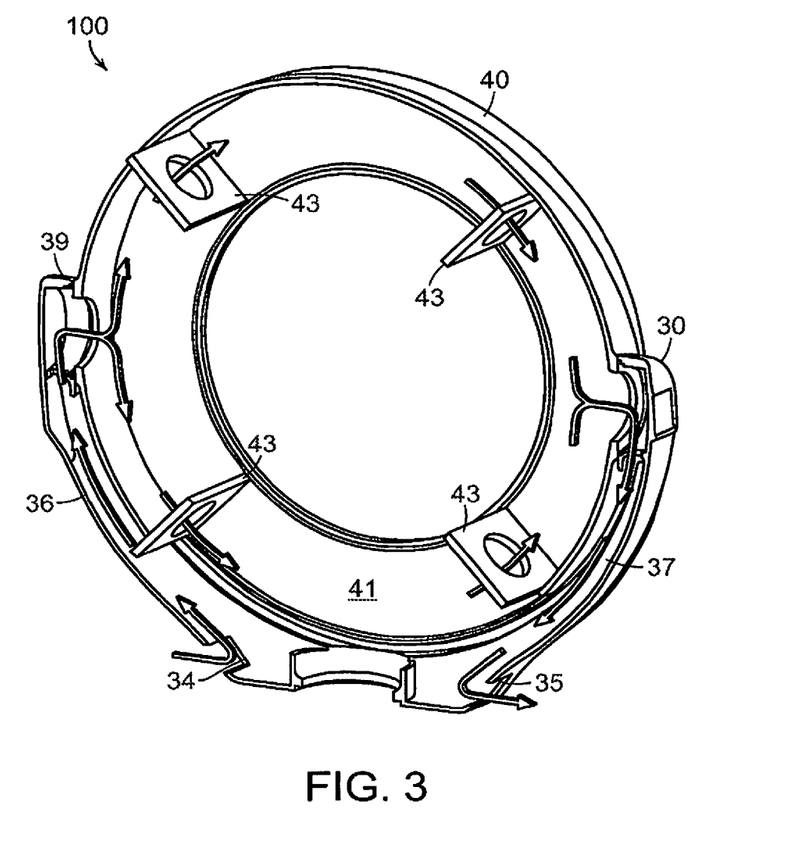
FIG. 3 is a cross-sectional perspective view of the gantry and gimbal of FIG. 2.

Within the gantry 40, a plurality of bulkheads 43 are provided in one embodiment to help direct the airflow in the desired pattern. The bulkheads 43 are mounted to the rotor 41, and generally divide the interior of the gantry 40 into a plurality of volume segments. Each bulkhead 43 can include one or more openings to permit air to flow through the bulkhead 43. A fan or blower 57(shown in FIG. 2) can be provided in the openings of the bulkheads 43 to direct the air to flow in the desired direction, and to prevent backflow of air in the opposite direction. One or more fans or blowers can be provided elsewhere in the gantry 40 to direct the flow of air in the desired pattern. Generally, at least two bulkheads 43 are provided on opposing sides of the gantry to provide the bifurcated air flow. Four or more bulkheads 43 may be provided, as is shown in FIGS. 2 and 3. The bulkheads 43 can comprise discrete components mounted to the rotor, such as the flat plates shown most clearly in FIG. 3. In some embodiments, the bulkheads 43 can be integrated with, and form part of, another component of the imaging system. For example, a bulkhead 43 similar to those shown in FIGS. 2 and 3 can also function as a part of the housing of an imaging component, such as a high-voltage generator or an on-board processing module (computer) for an x-ray CT scanner.

The imaging system generally operates in a conventional manner to obtain images of an object 56 (FIG. 2) located in the bore of the gantry. For example, in the case of an x-ray CT scan, the rotor 41 rotates within the housing of the gantry 40 while the imaging components, including the x-ray source and x-ray detector, obtain image data at a variety of scan angles. Generally, the system obtains image data over relatively short intervals, with a typical scan lasting less than a minute, or sometimes just a few seconds.

During these short intervals, however, a number of components, such as the x-ray source tube and the high-voltage generator, generate a massive amount of heat, which quickly diffuses through the gantry to heat up other components while the system is not in use. Accordingly, the airflow cooling system 80 of the invention is configured to manage and control the transfer of heat in the imaging system so as to avoid overheating and damage to the device, and further to minimize or eliminate the transfer of heat to heat-sensitive components on the gantry. In one aspect, the airflow cooling system 80 functions as a heat exchanger, taking in ambient air and circulating the air inside the interior of the gantry, where the air absorbs heat from the imaging components, and removing this heat from the system through the exhaust outlet.

The imaging system can be configured so that when the system is not obtaining image data, the rotor 41 rotates to the same "park" position within the gantry 40. During the intervals between scans, when the rotor is in the "park" position, a first group of imaging components are always located proximate the air intake side of the gantry 40, and a second group of imaging components are always located proximate the air outlet side of the gantry 40. As shown in FIG. 2, for example, the first group of imaging components can include the most heat sensitive components, and the second group can include the components that tend to generate the most heat.

Figure 4:
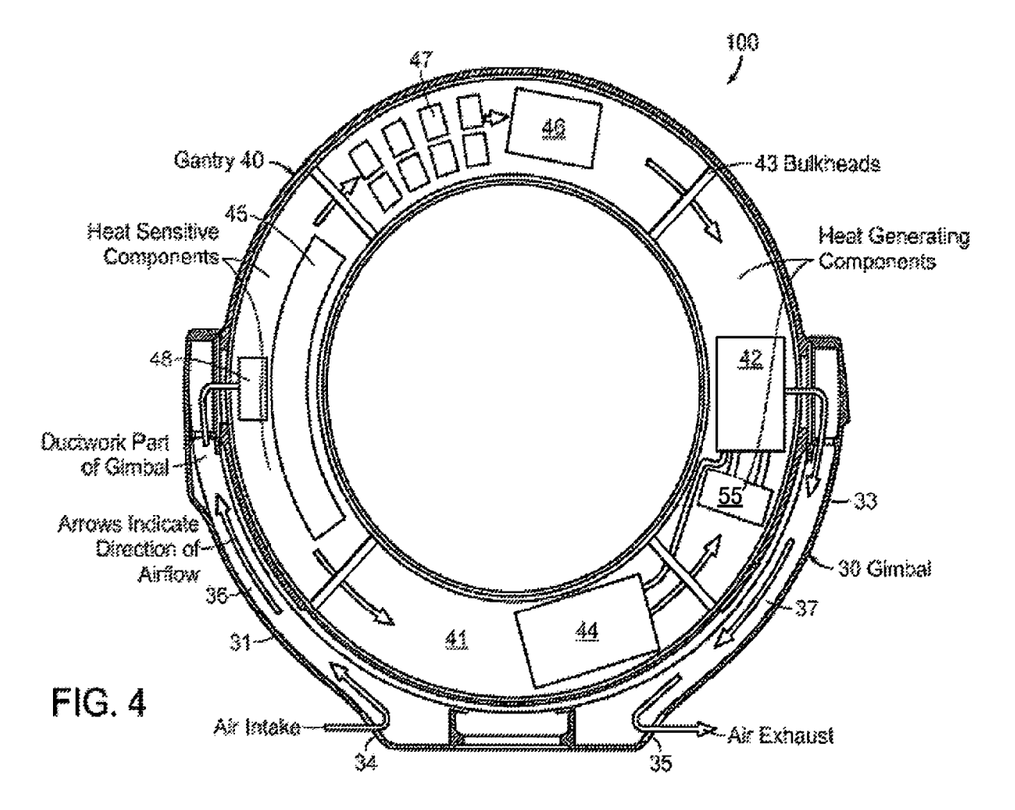
FIG. 4 is a cross-sectional schematic illustration of the arrangement of components in the gantry according to one embodiment.

FIG. 4 schematically illustrates an arrangement of components on the rotor 41 of an x-ray CT scanner according to one embodiment of the invention. In this embodiment, the imaging components include an x-ray source tube 42 and an x-ray detector array 45. These components are generally located opposite each other on the rotor 41. Other components include a high-voltage generator 44 that provides the high-voltage required to energize the x-ray tube 42, and a cooler system 45 that circulates a cooling fluid to the x-ray tube 42 to prevent the tube from overheating. These components are typically found in conventional x-ray CT scanning systems.

Other components on the rotor 41, however, are unique to the present system, and include a computer 45, a battery-based power supply 47, and a drive mechanism 48. The computer 45 is provided on-board the rotor 41 to provide at least some processing of the detected x-ray image data. The computer 45 can also provide system control functions. An advantage of providing the computer 45 on the rotor 41 is that it minimizes the data transfer requirements between the components located on the rotor 41 and processing and display devices located off the rotor 41. The power supply 47 can provide all the required power to the components on the rotor 41, and generally comprises a plurality of battery packs connected in series. The battery packs are preferably rechargeable, and are recharged during the "down-time" between image scans. A charger is provided on the gimbal 30, for example, and interfaces with the rotor 41 when the rotor is in the "park" position to recharge the battery packs. An advantage of the battery-based power supply 47 is that the conventional schemes for delivering power to the imaging components, such as complicated and expensive slip-ring systems and bulky cable systems, can be avoided. Similarly, placing the drive mechanism 48 on the rotor 41 helps cut down on the size and complexity of the imaging system, which is advantageous in terms of increasing the mobility of the system.

The various components on the rotor 41 can be considered in terms of both their sensitivity to heat, and the amount of heat they generate. In terms of sensitivity to heat, the most heat-sensitive component is the detector 45, the performance of which is known to be highly temperature-dependent. The battery-based power source 47 is also heat sensitive, as excessive heat can cause the battery packs to age prematurely. The computer 46 is both heat-sensitive and also generates some heat. The remaining components (x-ray tube 42, cooler 45, generator 44 and drive mechanism 48) are not particularly heat-sensitive. However, of these, the x-ray tube 42, cooler 45 and high voltage generator 44 are by far the biggest heat generators on the rotor 41. The drive mechanism 48 generates modest heat.

Accordingly, one suitable arrangement of the components on the rotor 41 is illustrated in FIG. 4. The rotor 41 is depicted in the "park" position, so that the cooling system can provide maximum cooling efficiency. As can be seen in FIG. 4, the detector array 45, which is highly heat-sensitive, is placed in close proximity to the air intake duct 36. In one embodiment, the detector array 45 is the closest component to the intake duct 36 so that the detector 45 receives generally the coolest air flow. The battery-based power supply 47 and the computer 46 are also provided on the air intake side of the rotor 41, downstream of the detector 45 and upstream of the components that generate the most heat. The largest heat generating components, including the x-ray tube 42 and associated cooler 55, and the high-voltage generator 44, are located on the air exhaust side of the rotor 41, in close proximity to the exhaust-side duct 37. In one embodiment, the x-ray tube 42 is located directly adjacent the entrance to exhaust duct 37, and is the component that is furthest downstream in the direction of the airflow within the gantry. In other embodiments, the x-ray tube cooler 45 can be located furthest downstream and adjacent the exhaust duct 37, as the cooler generally outputs a significant amount of heat from the tube 42. The bulkheads 43 can be provided in suitable locations on the rotor 41 to help isolate the more heat-sensitive components from the heat-generating components, and to minimize the backflow of heated air to the heat-sensitive components.

The location of the drive mechanism 48 is not critical, since it is neither particularly heat-generating nor particularly heat-sensitive. However, there may be some benefit to placing it away from the x-ray tube 42 to minimize EM interference with the tube which can affect the position of the x-ray focal spot. In this embodiment, the drive mechanism 48 is provided beneath the detector array 45, and 180 degrees away from the x-ray tube 42.

In certain embodiments, some components of the imaging system can be located on the gimbal 30. For example, some electronic control and processing circuitry, such as the battery charger, can be provided on the gimbal 30. As some of these electronic circuitry components can be sensitive to heat, they can be provided on the arm 31 of the gimbal 30 containing the air intake duct 26, and can be located within the intake duct 26, or in thermal communication with the intake duct 26.

As previously discussed, in certain embodiments the imaging system can be a mobile system that can be easily moved to different areas of a hospital and can be used at the point of care, such as in an operating room or emergency room. In many of these environments, the system will need to meet strict requirements for sterility. These requirements would not normally be applicable for the large, fixed devices currently found in a radiology department. One advantage of the present invention is that the airflow cooling system can provide effective cooling of the imaging components without interfering with the surgical sterile field. In general, when the imaging system is utilized in a surgical context, any part of the device that is exposed to the patient is considered to be within the "sterile field," and thus must be kept sterilized, draped or otherwise isolated to prevent contamination of the patient. This generally includes all exposed parts of the system that are located at the height of the patient table and above. In the present invention, the airflow cooling system is not exposed to the sterile field, since the only exposed parts of the cooling system are the air inlet opening 34 and air exhaust opening 35, which are located far below the patient table 60, preferably close to the ground, and generally direct the airflow away from the sterile field. It would not be acceptable to vent the airflow into the sterile field, since the air flows through the unsterilized interior of the gantry and could potentially carry germs or other contaminants into the sterile surgical field.

FIG. 5 illustrates an alternative embodiment of an imaging system 200 having a stand-alone gantry 40 with an airflow cooling system. The imaging system 200 is a magnetic resonance imaging system in this embodiment, although it will be understood that the same principles may be used in an x-ray CT imaging system. In this embodiment, the gantry 40 has a base portion 49 that can sit on the floor or other surface, and supports the generally O-shaped housing in which the rotor 41 and imaging components rotate. The air inlet opening 34, air exhaust opening 35 and ducts 36, 37 are provided in the gantry 40 itself, as opposed to in a separate gimbal structure. In other respects, the cooling system of this embodiment can function substantially as described in connection with FIGS. 1-4.

FIG. 6 illustrates another aspect of the present imaging system. In this embodiment, the gantry 40 is supported on a gimbal 30, and can tilt with respect to the gimbal. Here, the bottom of the gantry 40 is shown tilted upwards almost 90 degrees with respect to the gimbal. The bottom of the gantry 40 includes an opening 51 to permit easy access to the various imaging components housed within the gantry 40. Preferably, the opening 51 is sized to permit the imaging components to be removed from, or placed into, the interior of the gantry 40, as may be required for service, repair or periodic upgrades. In this embodiment, the opening 51 is sized to permit the detector array to pass through the opening, as the detector array is typically the largest component within the gantry. The internal gantry rotor can rotate within the gantry to allow any component to be accessed through the opening 51. An access panel (not shown) can be attached over the opening 51 to seal the gantry 40 during use. Certain components of the imaging system, including the detector array, for example, will generally be too large to be inserted or removed via the interior diameter of the gantry (i.e., through the gantry bore). The opening 51 can advantageously permit easy access to all of the components of the gantry. Although the opening 51 in this embodiment is illustrated as a single opening on the bottom side of the gantry, it will be understood that one or more access openings can be provided on any surface of the gantry, including at the top of the gantry.

Figure 7:
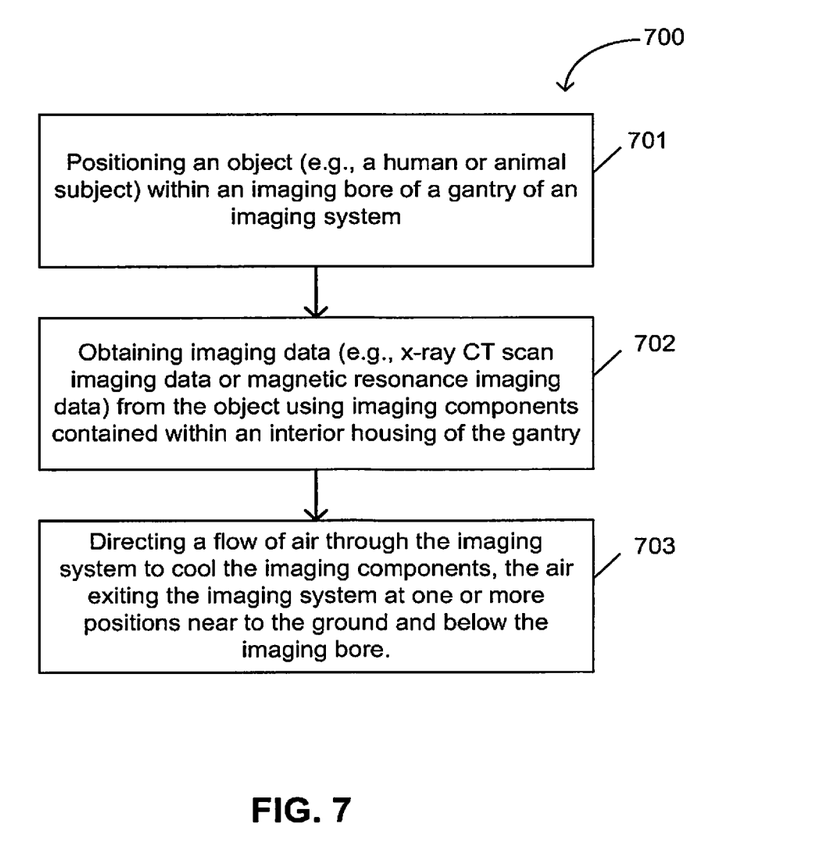
FIG. 7 is a process flow diagram illustrating an embodiment method for diagnostic imaging using an imaging system.

FIG. 7 is a process flow diagram illustrating an embodiment method 700 for diagnostic imaging using an imaging system, such as systems 100, 200 described above. In this embodiment, the method 700 includes positioning an object, such as a human or animal subject, within an imaging bore of a gantry of the imaging system (block 701), obtaining imaging data, such as x-ray CT scan imaging data or magnetic resonance imaging data, from the object using imaging components contained within an interior housing of the gantry (block 702), and directing a flow of air through the imaging system to cool the imaging components, the air exiting the imaging system at one or more positions near to the ground and below the imaging bore (block 703).

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims set forth below.

What is claimed is:

1. A mobile diagnostic imaging system, comprising:
   a mobile base;
   a gantry mounted above a surface of the base having an imaging bore and a housing defining an interior that contains imaging components; and
   an airflow cooling system that directs a flow of air through the interior of the housing of the gantry and includes an air intake opening and at least one air exhaust opening, wherein the at least one air exhaust opening directs all of the exhaust air exiting from the imaging system below a surgical sterile field.

2. The mobile diagnostic imaging system of claim 1, wherein the air intake opening and the at least one air exhaust opening are positioned near the ground and direct air flow below the surgical sterile field.

3. The mobile imaging system of claim 1, wherein the system comprises an x-ray CT imaging system.

4. The mobile imaging system of claim 1, wherein the system comprises a magnetic resonance imaging system.

5. The mobile imaging system of claim 1, wherein the gantry comprises a generally O-shaped housing that contains the imaging components.

6. A mobile diagnostic imaging system, comprising:
a mobile base;
a gantry mounted above a surface of the base having an imaging bore and a housing defining an interior that contains imaging components; and
an airflow cooling system that directs a flow of air through the interior of the housing of the gantry and includes an air intake opening and an air exhaust opening, wherein the air exhaust opening directs the exhaust air exiting from the imaging system below a surgical sterile field, and the airflow cooling system further comprises an air duct system located at least partially external to the housing of the gantry that provides a fluid connection between the air intake opening and the interior of the housing of the gantry at a first side of the gantry, and provides fluid connection between the air exhaust opening located below the surgical sterile field and the interior of the housing of the gantry at a second side of the gantry, opposite the first side.

7. The mobile imaging system of claim 6, wherein the gantry is supported by a gimbal, and the duct system is provided in the gimbal.

8. The mobile imaging system of claim 6, wherein the duct system is provided in the gantry.

9. The mobile imaging system of claim 7, further comprising a bearing system with a through-hole that connects the gimbal to the gantry on the two opposing sides of the gantry and allows the gantry to tilt relative to the gimbal.

10. The mobile imaging system of claim 9, wherein the airflow directed from the intake opening on the gimbal is directed to enter through the bearing attached to the gantry to enter the gantry at an intake side and wherein the airflow passes through the generally O-shaped gantry and exits through the bearing attached to the gantry opposite the first bearing thereby allowing the airflow to be directed through an exhaust opening on the gimbal.

11. The mobile imaging system of claim 1, further comprising an airflow bifurcation system located within gantry that forces airflow entering a first side of the gantry to be distributed in two directions around the interior of the gantry and exit through a second side of the gantry, opposite the first side.

12. The mobile imaging system of claim 11, wherein the bifurcation system comprises a plurality of bulkheads that direct the air along the two directions of the gantry and prevent airflow in the opposing direction.

13. The mobile imaging system of claim 12, wherein at least one fan is provided within the gantry to direct the airflow.

14. The mobile imaging system of claim 13, wherein the at least one fan is cooperatively associated with the bulkheads.

15. The mobile imaging system of claim 1, further comprising a rotor that rotates around the interior of the gantry, the imaging components being mounted to the rotor.

16. The mobile imaging system of claim 15, further comprising a plurality of bulkheads mounted to the rotor.

17. The mobile imaging system of claim 1, wherein heat sensitive imaging components are placed generally adjacent to another on the gantry such that when the imaging system is not in use, the heat sensitive components are located proximate an air intake side of the gantry and less heat sensitive components are located proximate an air exhaust side of the gantry.

18. The mobile imaging system of claim 7, wherein at least some imaging components are provided on the gimbal, and the heat sensitive components are generally placed proximate the air intake opening and the less heat sensitive components are generally placed proximate the air exhaust opening.

19. The mobile imaging system of claim 17, wherein heat generating imaging components are generally placed as closed to the air exhaust as possible.

20. The mobile imaging system of claim 17, wherein the gantry is enclosed or sealed.

21. The mobile imaging system of claim 1, wherein the gantry has one or more openings on an outer diameter of the gantry for installation, removal and servicing of components within the gantry.

22. A mobile diagnostic imaging system, comprising:
a mobile base;
a gantry mounted above a surface of the base having an imaging bore and a housing defining an interior that contains imaging components; and
an airflow cooling system that directs a flow of air through the interior of the housing of the gantry and includes an air intake opening and an air exhaust opening, wherein the air exhaust opening directs the exhaust air exiting from the imaging system below a surgical sterile field, and the air intake opening and an air exhaust opening are positioned below an imaging region defined by the gantry.

23. The mobile imaging system of claim 17, wherein the heat sensitive components include a detector array.

24. The mobile imaging system of claim 17, wherein the heat sensitive components include at least one of a battery power source and a computer.

25. The mobile imaging system of claim 19, wherein the heat generating components include at least one of an x-ray source, a high-voltage generator, and an x-ray tube cooler.

26. A method for diagnostic imaging using a mobile imaging system, the mobile imaging system comprising a first portion comprising a gantry and a second portion that supports the gantry, the method comprising:
positioning an object within an imaging bore of the gantry of the mobile imaging system;
obtaining imaging data from the object using imaging components contained within an interior housing of the gantry; and
directing a flow of air through the mobile imaging system to cool the imaging components, wherein all of the air exiting the mobile imaging system exits the mobile imaging system at one or more positions below a surgical sterile field.

27. A method for diagnostic imaging using a mobile imaging system, the mobile imaging system comprising a first portion comprising a gantry and a second portion that supports the gantry, the method comprising:
positioning an object within an imaging bore of the gantry of the mobile imaging system;
obtaining imaging data from the object using imaging components contained within an interior housing of the gantry; and
directing a flow of air through the mobile imaging system to cool the imaging components, the air exiting the mobile imaging system at one or more positions below a surgical sterile field, wherein the air enters and exits the imaging system at positions below the imaging bore of the gantry.

28. The method of claim 26, further comprising:
directing the flow of air through the interior housing of the gantry.

29. The method of claim 26, further comprising:
rotating a rotor within the gantry housing to a stationary park position when the imaging system is not obtaining imaging data, the imaging components being mounted to the rotor.

30. A method for diagnostic imaging using a mobile imaging system, the mobile imaging system comprising a first portion comprising a gantry and a second portion that supports the gantry, the method comprising:
positioning an object within an imaging bore of the gantry of the mobile imaging system;
obtaining imaging data from the object using imaging components contained within an interior housing of the gantry;
rotating a rotor within the gantry housing to a stationary park position when the imaging system is not obtaining imaging data, the imaging components being mounted to the rotor, and the rotor is rotated to a stationary park position in which heat sensitive imaging components are positioned on an upstream side of the flow of air and heat generating imaging components are positioned on a downstream side of the flow of air; and
directing a flow of air through the mobile imaging system to cool the imaging components, the air exiting the mobile imaging system at one or more positions below a surgical sterile field.

31. A method for diagnostic imaging using a mobile imaging system, the mobile imaging system comprising a first portion comprising a gantry and a second portion that supports the gantry, the method comprising:
positioning an object within an imaging bore of the gantry of the mobile imaging system;
obtaining imaging data from the object using imaging components contained within an interior housing of the gantry; and
directing a flow of air through the mobile imaging system to cool the imaging components, the air exiting the mobile imaging system at one or more positions below a surgical sterile field, wherein directing the flow of air through the mobile imaging system further comprises directing the flow of air through a duct system that is at least partially external to the interior housing of the gantry and provides fluid communication between the interior housing of the gantry and at least one air exhaust opening located below the surgical sterile field.

32. The method of claim 31, wherein the duct system is contained in a gimbal structure that supports the gantry.

33. The method of claim 28, further comprising:
directing the flow of air in two directions around the interior of an O-shaped gantry.

34. The method of claim 26, wherein the object comprises a human or animal subject.

35. The method of claim 26, wherein the imaging data comprises x-ray CT scan imaging data.

36. The method of claim 26, wherein the imaging data comprises magnetic resonance imaging data.

37. The mobile imaging system of claim 1, wherein a portion of the system including the gantry translates with respect to the base and at least one of the air intake opening and the at least one air exhaust opening are located on the portion of the system that translates with respect to the base.

38. The method of claim 26, further comprising:
translating the first portion of the imaging system comprising the gantry relative to a base of the imaging system, wherein the air enters and exits the imaging system at one or more positions on the first portion of the system.

* * * * *